United States Patent [19]

Belletire et al.

[11] 4,283,409

[45] Aug. 11, 1981

[54] IMIDAZOLONE DERIVATIVES

[75] Inventors: John L. Belletire, Madison, Wis.; Reinhard Sarges, Mystic, Conn.

[73] Assignee: Pfizer Inc., New York, N.Y.

[21] Appl. No.: 89,655

[22] Filed: Oct. 29, 1979

[51] Int. Cl.³ .......................................... A61K 31/415
[52] U.S. Cl. .............................. 424/273 R; 424/256; 424/258; 546/15; 548/301
[58] Field of Search ...................... 424/273 R; 548/301

[56] References Cited

U.S. PATENT DOCUMENTS 3,821,383  6/1974  Sestanj et al. .................... 424/258

OTHER PUBLICATIONS

Granger et al. Chem. Abst. vol. 70, 1969, 24392a.

Faust et al. Jour. of the Ameri. Pharmaceutical Association vol. 46, No. 2, pp. 118–123, 1957.

*Primary Examiner*—Henry R. Jiles
*Assistant Examiner*—Jane T. Fan
*Attorney, Agent, or Firm*—Francis X. Murphy; Charles J. Knuth; Peter C. Richardson

[57]         ABSTRACT

A series of novel spiro-imidazolone compounds and their pharmaceutically acceptable acid addition salts are disclosed. These particular compounds are useful in therapy as agents for the control of certain chronic diabetic complications. 3′,4′-Dihydro-spiro-[imidazolidine-4,1′(2′H)naphthalene]-5-one represents a typical and preferred member compound. Methods for preparing all these compounds from known hydantoin starting materials are provided.

4 Claims, No Drawings

IMIDAZOLONE DERIVATIVES

BACKGROUND OF THE INVENTION

This invention relates to new and useful imidazolone derivatives of principal interest to those in the field of medicinal chemistry and/or chemotherapy. More particularly, it is concerned with a novel series of spiro-imidazolone compounds, which are of especial value in view of their ability to effectively control certain chronic complications arising from diabetes mellitus (e.g., diabetic cataracts, retinopathy and neuropathy). The invention also includes a new method of therapy within its scope.

In the past, various attempts have been made by numerous investigators in the field of organic mdicinal chemistry to obtain new and better oral antidiabetic agents. For the most part, these efforts have involved the testing of various organic compounds in an endeavor to determine their ability to lower blood sugar (i.e., glucose) levels. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 to disclose that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductace, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of various diabetic subjects are thereby prevented or reduced. As a result, these compounds control certain chronic diabetic complications, including those of an ocular nature, since it is already known in the art that the presence of polyols in the lens of the eye quite often leads to cataract formation and concomitant loss of lens clarity.

SUMMARY OF THE INVENTION

In accordance with the present invention, it has now been rather surprisingly found that various novel spiro-imidazolone compounds are extremely useful when employed in therapy as agents for the control of certain chronic complications arising in a diabetic subject even though they are not outstanding aldose reductase inhibitors per se. More specifically, the novel compounds of this invention are all selected from the group consisting of spiro-imidazolone bases of the formulae:

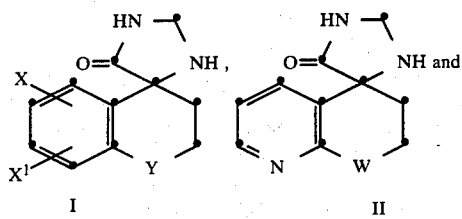

-continued

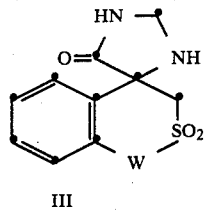

III and the pharmaceutically acceptable acid addition salts thereof, wherein W is $-(CH_2)_n-$; X is hydrogen and $X^1$ is hydrogen, fluorine, chlorine, bromine, lower alkyl or lower alkyl, or X and $X^1$, when taken separately, are each chlorine, lower alkyl or lower alkoxy, and then taken together are $-OCH_2(CH_2)_nO-$; Y is W, oxygen, sulfur, oxosulfur or dioxosulfur; and n is zero or one. These novel compounds possess the ability to markedly reduce or even inhibit sorbitol accumulation in the lens and peripheral nerves of various diabetic subjects. A typical and preferred member compound of the invention is 3',4'-dihydro-spiro-[imidazolidine-4,1'(2'H)naphthalene]-5-one. This particular compound is remarkably effective in lowering sorbitol levels in the lens and sciatic nerve of diabetic subjects and galactitol levels in the lens of galactosemic subjects to a high degree.

DETAILED DESCRIPTION OF THE INVENTION

In accordance with the process employed for preparing the novel compounds of this invention, an appropriate spiro-hydantoin compound of the formulae:

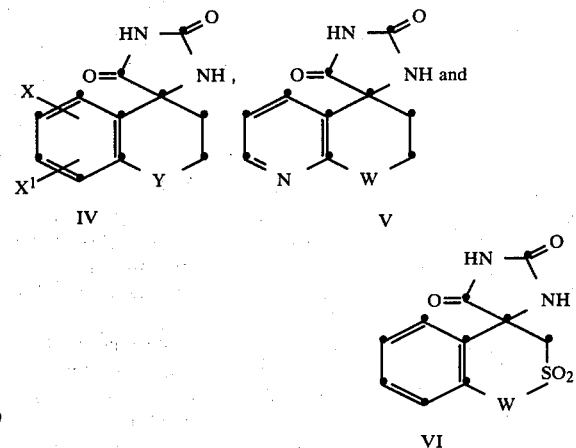

wherein W, X, $X^1$ and Y are all as previously defined, is hydrolyzed preferably with the aid of an alkali metal or alkaline-earth metal hydroxide to yield the corresponding alicyclic (or heterocyclic) α-amino acid (e.g., 1-amino-1,2,3,4-tetrahydro-1-naphthoic acid), which is then reacted with thiourea in a conventional manner to afford the corresponding 2-thiohydantoin, followed by reduction and/or desulfurization of the latter compound with a suitable agent such as Raney nickel or metallic sodium in a lower alkanol solvent medium (preferably using a lower alkanol containing one to six carbon atoms) to ultimately yield the desired spiro-imidazolone final product of the structural formulae previously indicated. In practice, the last step of the process is usually conducted at the reflux temperature of the reaction mixture. In this way, 3',4'-dihydro-spiro-

[imidazolidine-4'1'(2'H)naphthalene]-2,5-dione is converted via 1-amino-1,2,3,4-tetrahydro-1-naphthoic acid and 3',4'-dihydro-spiro-[imidazolidine-4,1'(2H)naphthalene]-5-one-2-thione, respectively, to 3',4'-dihydro-spiro-[imidazolidine-4,1'(2'H)naphthalene]-5-one per se.

Alternatively, the alicyclic (or heterocyclic) α-amino acid used in the above reaction schem (second step of overall process) can also be prepared by treating the corresponding carbonyl ring compound (the preparation of which is hereinafter discussed) with sodium cyanide and ammonium chloride in a modified Strecker synthesis, followed by hydrolysis of the resulting α-amino nitrile intermediate to give the corresponding α-amino acid having the desired alicyclic (or heterocyclic) ring structure.

The spiro-hydantoin compounds used as starting materials in the first step of the overall principal process of this invention (viz., those of structural formulae IV—VI) are all readily synthesized by first condensing the appropriate carbonyl ring compound, such as the corresponding 1-indanone, 1-tetralone, 4-chromanone, thiochroman-4-one, 7,8-dihydroquinolin-5(6H)-one, 6,7-dihydropyrindin-5-(5H)-one, thioindane-3-one-1,1-dioxide and 4-oxoisothiochroman-2,2-dioxide, of the respective formulae:

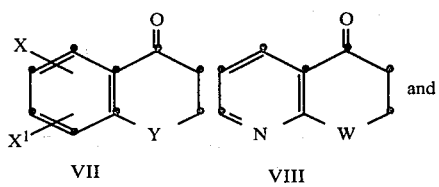

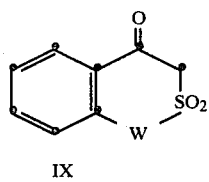

wherein W, X, $X^1$, and Y are, again, all as previously defined, with an alkali metal cyanide (e.g., sodium cyanide or potassium cyanide) and ammonium carbonate to form the desired spiro-hydantoin intermediate product of the structural formulae previously indicated. This particular reaction is normally carried out in the presence of a reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diethylformamide and N,N-dimethylacetamide, etc. In general, the reaction is conducted at a temperature that is in the range of from about 20° C., up to about 150° C. for a period of about two hours to about four days. Although the amount of reactant and reagents employed in the reaction can very to some extent, it is preferable to employ at least a slight molar excess of the alkali metal cyanide reagent with respect to the carbonyl ring compound starting material in order to effect maximum yield. Upon completion of the reaction, the desired product is easily isolated in a conventional manner, e.g., by first diluting the reaction mixture with water (boiling if necessary) and then cooling the resultant aqueous solution to room temperature, followed by acidification to afford the particular spiro-hydantoin compound in the form of a readily-recoverable precipitate.

Compounds of the invention in which Y of formula I is

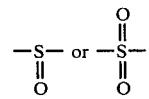

can be prepared from those compounds wherein Y is sulfur by merely oxidizing the latter group of compounds in accordance with standard techniques well known to those skilled in the art. For instance, the use of sodium periodate in this connection leads to the formation of the oxosulfur compounds, while peroxy acids like peracetic acid, perbenzoic acid and m-chloroperoxybenzoic acid, etc., are preferably employed to afford the corresponding dioxosulfur compounds. On the other hand, certain compounds of the invention having a ring substituent (X, $X^1$, etc.) which is halogen (as previously defined) may alternatively be prepared from the corresponding unsubstituted compounds wherein at least one of X and $X^1$ is hydrogen by means of direct halogenation techniques well known to those in the field of synthetic organic chemistry.

The ketone starting materials (i.e., carbonyl ring compounds) required for preparing the spiro-hydantoin intermediates of this invention are, for the most part, known compounds and are either readily available commercially, like 1-indanone and 6-chloro-4-chromanone, etc., or else they can easily be synthesized by those skilled in the art starting from common chemical reagents and using conventional methods of organic synthesis. For instance, 6-fluoro-4-chromanone is obtained by condensing β-(p-fluorophenoxy)propionic acid in the presence of polyphosphoric acid, while 6,7-dichlorothiochroman-4-one is obtained by condensing β-(3,4-dichlorophenylthio)propionic acid in the presence of concentrated sulfuric acid. In both cases, the starting organic acid is ultimately derived from a commercially available compound.

The pharmaceutically acceptable acid addition salts of the spiro-imidazolone base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinic, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt is readily obtained.

As previously indicated, the spiro-imidazolone compounds of this invention readily reduce lens sorbitol levels in diabetic subjects. For instance, 3',4'-dihydro-spiro-[imidazolidine-4,1'(2'H)naphthalene]-5-one, a typical and preferred agent of the present invention, has been found to inhibit the formation of sorbitol levels in diabetic rats to a significantly high degree (52%) when given by the oral route of administration at a dose level of 25 mg./kg. without showing any substantial signs of toxic side effects. The herein described compounds can be administered by either the oral or parenteral routes of administration without causing any significant untoward pharmacological side reactions to occur. These compounds are ordinarily administered in dosages ranging from about 0.50 mg. to about 50 mg. per kg. of body weight per day, although variations will necessarily occur depending upon the weight and condition of the subject being treated and the particular route of administration chosen.

The spiro-imidazolone compounds of this invention may be administered either alone or in combination with pharmaceutically acceptable carriers, and such administration can be carried out in both single and multiple dosages. The compounds of this invention can be administered in a wide variety of dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. The oral pharmaceutical formulations can be suitably sweetened and/or flavored by means of various agents of the type commonly employed for such purposes. In general, the compounds of the invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various combinations thereof.

For parenteral administration, solutions of these spiro-imidazolones in sesame or peanut oil or in aqueous propylene glycol or N,N-dimethylformamide may be employed, as well as sterile aqueous solutions of the corresponding water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. The sterile aqueous media employed are all readily obtainable by standard techniques well-known to those skilled in the art. Additionally, it is also possible to administer the aforesaid spiro-imidazolone compounds topically via an appropriate ophthalmic solution which can then be applied dropwise to the eye.

The activity of the compounds of the present invention, as agents for the control of chronic diabetic complications, is determined by their ability to successfully pass one or more of the following standard biologically and/or pharmacological tests, viz., (1) measuring their ability to reduce or inhibit sorbitol accumulation in the sciatic nerve of acutely streptozotocinized (i.e., diabetic) rats; (2) measuring their ability to reverse already-elevated sorbitol levels in the sciatic nerve and lens of chronic streptozotocin-induced diabetic rats; (3) measuring their ability to prevent or inhibit galactitol formation in the lens of acutely galactosemic rats, and (4) measuring their ability to delay cataract formation and reduce the severity of lens opacities in chronic galactosemic rats.

EXAMPLE 1

A mixture consisting of 12.5 g. (0.058 mole) of 3',4'-dihydro-spiro-[imidazolidine-4,1'(2'H)naphthalene]-2,5-dione [*Chemical Abstracts*, Vol. 35, p. 6576$^7$ (1941)] and 54.6 g of barium hydroxide hexahydrate in 75 ml of water was refluxed for a period of 24 hours and then cooled to room temperature ($\sim$25° C.). The pH of the resulting solution was then adjusted to pH 7.0 with the aid of concentrated sulfuric acid and thereafter filtered. The filtrate was then readjusted to pH 5.0 and freeze-dried to give 6.0 g. of crude 1-amino-1,2,3,4-tetrahydro-1-naphthoic acid (m.p. 247°–248° C.). Conversion of the later substance to the corresponding hydrochloride salt was then accomplished by dissolving a 1.0 g. sample of the crude material in ethanol and saturating same with dry hydrogen chloride gas, followed by evaporation to give a residue containing the crude salt, which was then slurried with diethyl ether and filtered to ultimately yield 759 mg. of the desired hydrochloride (m.p. 268°–270° C.). Recrystallization of the latter material from methanol-diethyl ether then gave 344 mg. of pure 1-amino-1,2,3,4-tetrahydro-1-naphthoic acid hydrochloride, m.p. 275°–277° C.

Anal. Calcd for $C_{11}H_{13}NO_2\cdot HCl$: C, 58.03; H, 6.19; N, 6.15. Found: C, 57.60; H, 6.29; N, 6.09.

A mixture consisting of 3.82 g. (0.020 mole) of 1-amino-1,2,3,4-tetrahydro-1-naphthoic acid and 6.24 g (0.082 mole) of thiourea was heated to 210° C. for a period of three hours, during which time the mixture liquified and ammonia rapidly evolved therefrom. At the end of this time, the spent reaction was cooled to room temperature ($\sim$25° C.) and acidified with 3 N hydrochloric acid, followed by extraction with ethyl acetate. The ethyl acetate layer was separated and washed with 1 N aqueous sodium hydroxide, and the resulting aqueous layer was saved and subsequently acidified with 3 N hydrochloric acid to a pH of 5.0. The precipitated solids obtained in this manner were then extracted with fresh ethyl acetate and the latter organic extracts were combined, filtered and subsequently evaporated to near dryness while under reduced pressure to afford 1.6 g. (35%) of pure 3',4'-dihydro-spiro-[imidazolidine-4,1'(2'H)naphthalene]-5-one-2-thione as the residue.

In a flame-dried reaction flask containing 10 ml. of freshly distilled isoamyl alcohol, there were placed 300 mg. (0.00129 mole) of 3',4'-dihydro-spiro-[imidazolidine-4,1'(2'H)naphthalene]-2-one-5-thione (prepared as described above) while the entire system was under a dry nitrogen atmosphere. The resulting solution was then treated with 0.5 g. of sodium, which was added in small portions, and the mixture so obtained was heated at 90°–100° C. for a period of 30 minutes. After cooling to room temperature (~25° C.), the excess sodium was destroyed with 10 ml. of methanol and the spent reaction mixture was diluted with water and subsequently extracted with three separate fresh portions of benzene. The combined benzene layers were then washed with water, dried over anhydrous magnesium sulfate and filtered. The resulting filtrate was thereafter evaporated to near dryness while under reduced pressure and the residue so obtained was slurried with diethyl ether and 1 N hydrochloric acid, followed by basification of the aqueous layer with 4 N aqueous potassium hydroxide. Extraction of the latter basified solution with methylene chloride then gave a clear organic extract, which was subsequently washed with water and dried over anhydrous magnesium sulfate. After removal of the drying agent by means of filtration and the solvent by means of evaporation under reduced pressure, there was finally obtained 78 mg. (30%) of crude 3′,4′-dihydro-spiro-[imidazolidine-4,1′(2′H)naphthalene]-5-one as the desired final product. Recrystallization of the latter material from ethanol then gave analytically pure 3′,4′-dihydro-spiro-[imidazolidine-4,1′(2′H)naphthalene]-5-one, m.p. 181°–183° C.

Anal. Calcd for $C_{12}H_{14}N_2O$: C, 71.26; H, 6.98; N, 13.85. Found: C, 70.80; H, 6.98; N, 13.71.

EXAMPLE 2

The following spiro-imidazolone compounds may be prepared by employing the procedures described in Example 1, starting from the corresponding spiro-hydantoin compound in each instance and proceeding through the corresponding alicyclic (or heterocyclic) α-amino acid and 2-thiohydantoin intermediates, respectively:

spiro-[imidazolidine-4,1′-indan]-5-one
6′-methoxy-spiro-[imidazolidine-4,1′-indan]-5-one
6′-fluoro-spiro-[imidazolidine-4,1′-indan]-5-one
5′,6′-dimethoxy-spiro-[imidazolidine-4,1′-indan]-5-one
5′,6′-methylenedioxy-spiro-[imidazolidine-4,1′-indan]-5-one
5′-methoxy-spiro-[imidazolidine-4,1′ indan]-5-one
6′-chloro-spiro-[imidazolidine-4,1′-indan]-5-one
6′-bromo-spiro-[imidazolidine-4,1′-indan]4,1′-indan]-5-one
5′-methyl-spiro-[imidazolidine-4,1′-indan]-5-one
6′-(n-butyl)-spiro-[imidazolidine-4,1′-indan]-5-one
5′,6′-dichloro-spiro-∂imidazolidine-4,1′-indan]-5-one
5′,6′-dimethyl-spiro-[imidazolidine-4,1′-indan]-5-one
3′,4′-dihydro-7′-methoxy-spiro-[imidazolidine-4,1′(2′H)naphthalene-5-one
3′,4′-dihydrox-6′,7′-dimethoxy-spiro-[imidazolidine-4,1′(2′H)naphthalene]-5-one
3′,4′-dihydro-6′-methoxy-spiro-[imidazolidine-4,1′(2′H)naphthalene]-5-one
3′,4′-dihydro-5′-methoxy-spiro-[imidazolidine-4,1′(2′H)naphthalene]-5-one
3′,4′-dihydro-7′-fluoro-spiro-[imidazolidine-4,1′(2′H)naphthalene]-5-one
3′,4′-dihydro-7′-chloro-spiro-[imidazolidine-4,1′(2′H)naphthalene]-5-one
3′,4′-dihydro-6′-bromo-spiro-[imidazolidine-4,1′(2′H)naphthalene]-5-one
3′,4′-dihydro-6′-methyl-spiro-[imidazolidine-4,1′(2′H)naphthalene]-5-one
3′,4′-dihydro-7′-(n-butoxy)-spiro-[imidazolidine-4,1′(2′H)naphthalene]-5-one
3′,4′-dihydro-6′,7′-dichloro-spiro-[imidazolidine-4,1′(2′H)naphthalene]-5-one
3′,4′-dihydro-6′,7′-diethyl-spiro-[imidazolidine-4,1′(2′H)naphthalene]-5-one
3′,4′-dihydro-6′,7′-dimethoxy-spiro-[imidazolidine-4,1′(2′H)naphthalene]-5-one
3′,4′-dihydro-6′,7′-ethylenedioxy-spiro-[imidazolidine-4,1′(2′H)naphthalene]-5-one
spiro-[chroman-4,4′-imidazolidine]-5′-one
6-methoxy-spiro-[chhroman-4,4′-imidazolidine]-5′-one
6′-fluoro-spiro-[chroman-4,4′-imidazolidine]-5′-one
6′,7′-dichloro-spiro-[chroman-4,4′-imidazolidine]-5′-one
6′,8′-dichloro-spiro-[chroman-4,4′-imidazolidine]-5′-one
6-chloro-spiro-[chroman-4,4′-imidzolidine]-5′-one
8-chloro spiro-[chroman-4,4′-imidazolidine]-5′-one
6-bromo-spiro-[chroman-4,4′-imidazolidine]-5′-one
6,8-dimethyl-spiro-[chroman-4,4′-imidazolidine]-5′-one
6-(n-butyl)-spiro-[chroman-4,4′-imidazolidine]-5′-one
7-methyl-spiro-[chroman-4,4′-imidazolidine]-5-one
6-(n-butoxy)-spiro-[chroman-4,4′-imidazolidine]-5′-one
6,7-dimethoxy-spiro-[chroman-4,4′-imidazolidine]-5′-one
6,7-ethylenedioxy-spiro-[chroman-4,4′-imidazolidine]-5′-one
spiro-[imidazolidine,-4,4′-thiochroman]-5-one
6′-methoxy-spiro-[imidazolidine-4,4′-thiochroman]-5-one
6′-chloro-spiro-[imidazolidine-4,4′-thiochroman]-5-one
6′-bromo-spiro-[imidazolidine-4,4′-thiochroman]-5-one
6′,7′-dichloro-spiro-[imidazolidine-4,4′-thiochroman]-5-one
6′-fluoro-spiro-[imidazolidine-4,4′-thiochroman]-5-one
8′-chloro-spiro-[imidazolidine-4,4′-thiochroman]-5-one
7′-chloro-spiro-[imidazolidine-4,4′-thiochroman]-5-one
6′-methyl-spiro-[imidazolidine-4,4′-thiochroman]-5-one
7′-(n-butyl)-spiro-[imidazolidine-4,4′-thiochroman]-5-one
7′-(n-butoxy)-spiro-[imidazolidine-4,4′-thiochroman]-5-one
6′,8′-dichloro-spiro-[imidazolidine-4,4′-thiochroman]-5-one
6′,7′-dimethyl-spiro-[imidazolidine-4,4′-thiochroman]-5-one
6′,7′-dimethoxy-spiro-[imidazolidine-4,4-thiochroman]-5-one
6′,7′-diethoxy-spiro-[imidazolidie-4,4′-thiochroman]-5-one
6′,7′-methylenedioxy-spiro-[imidazolidine-4,4′-thiochroman]-5-one
6′,7′-ethylenedioxy-spiro-[imidazolidine-4,4′-thiochroman]-5-one
spiro-[imidazolidine-4,4′-thiochroman]-5-one-1′-oxide
6′-fluoro-spiro-[imidazolidine-4,4′-thiochroman]-5-one-1′-oxide
8′-chloro-spiro-[imidazolidine-4,4′-thiochroman]-5-one-1′-oxide
6′-bromo-spiro-[imidazolidine-4,4′-thiochroman]-5-one-1′-oxide
6′-methyl-spiro-[imidazolidine-4,4′-thiochroman]-5-one-1′-oxide
6′-methoxy-spiro-[imidazolidine-4,4′-thiochroman]-5-one-1′-oxide
6′,7′-dichloro-spiro-[imidazolidine-4,4′-thiochroman]-5-one-1′-oxide
6′,7′-dimethyl-spiro-[imidazolidine-4,4′-thiochroman]-5-one-1′-oxide 6',7'-dimethoxy-spiro-[imidazolidine-4,4'-thiochroman]-5-one-1'-oxide 6',7'-methylenedioxy-spiro-[imidazolidine-4,4'-thiochroman]-5-one-1'-oxide spiro-[imidazolidine-4,4'-thiochroman]-5-one-1',1'-dioxide 6'-fluoro-spiro-[imidazolidine-4,4'-thiochroman]-5-one-1',1'-dioxide 8'-chloro-spiro-[imidazolidine-4,4'-thiochroman]-5-one-1',1'-dioxide 6'-methyl-spiro-[imidazolidine-4,4'-thiochroman]-5-one-1',1'-dioxide 6'-methoxy-spiro-[imidazolidine-4,4'-thiochroman]-5-one-1',1'-dioxide 6',7'-dichloro-spiro-[imidazolidine-4,4'-thiochroman]-5-one-1',1'-dioxide 6',7'-dimethyl-spiro-[imidazolidine-4,4'-thiochroman]-5-one-1',1'-dioxide 6',7'-dimethoxy-spiro-[imidazolidine-4,4'-thiochroman]-5-one-1',1'-dioxide 6',7'-methylenedioxy-spiro-[imidazolidine-4,4'-thiochroman]-5-one-1',1'-dioxide spiro-[imidazolidine-4,4'-isothiochroman]-5-one-1',1'-dioxide 7',8'-dihydro-spiro-[imidazolidine-4,5'(6H)-quinoline]-5-one 6',7'-dihydro-spiro-[imidazolidine-4,5'(5H)-pyrindine]-5-one

EXAMPLE 3

The non-toxic hydrohalide acid addition salts of each of the previously reported spiro-imidazolone base compounds of this invention, such as the corresponding novel hydrochloride, hydrobromide and hydroiodide salts, may be prepared by dissolving the respective organic base compound in absolute ether followed by the introduction of the appropriate hydrohalide gas into the reaction solution until saturation of same is complete with respect to said gas, whereupon the desired acid addition salt precipitates from said solution. In this way, 50 mg. of 3',4'-dihydro-spiro-[imidazolidine-4,1'(2'H)naphthalene]-5-one, obtained as a free base product in Example 1, is converted via dry hydrogen chloride gas to the corresponding hydrochloride acid addition salt in substantially quantitative yield.

EXAMPLE 4

The nitrate, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts of each of the aforementioned spiro-imidazolone base compounds reported previously may be prepared by dissolving equimolar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of 3',4'-dihydro-spiro-[imidazolidine-4,1'(2'H)naphthalene]-5-one and concentrated sulfuric acid react to afford the corresponding sulfuric acid addition salt.

EXAMPLE 5

A dry solid pharmaceutical composition is prepared by blending the following materials together in the proportions by weight specified below:

| | |
|---|---|
| 3',4'-Dihydro-spiro-[imidazolidine-4,1'(2'H)naphthalene]-5-one | 50 |
| Sodium citrate | 25 |
| Alginic acid | 10 |
| Polyvinylpyrrolidone | 10 |
| Magnesium stearate | 5 |

After the dried compound is thoroughly blended, tablets are punched from the resulting mixture, each tablet being of such size that it contains 200 mg. of the active ingredient. Other tablets are also prepared in a similar fashion containing 25, 50 and 100 mg. of the action ingredient, respectively, by merely using the appropriate amount of the spiro-imidazolone compound in each case.

EXAMPLE 6

A dry solid pharmaceutical composition is prepared by combining the following materials together in the proportions by weight indicated below:

| | |
|---|---|
| 3',4'-Dihydro-spiro-[imidazolidine-4,1'(2'H)naphthalene]-5-one | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE 7

The final product of Example 1, viz., 3',4'-dihydro-spiro-[imidazolidine-4,1'(2'H)naphthalene]-5-one, was tested for its ability to reduce or inhibit sorbitol accumulation in the sciatic nerve of streptozotocinized (i.e., diabetic rats) by the procedure essentially described in U.S. Pat. No. 3,821,383. In the present study, the amount of sorbitol accumulation in the sciatic nerves was measured 27 hours after the induction of diabetes. The compound was then administered orally at 25 mg./kg. at intervals of 4, 8 and 24 hours after the administration of streptozotocin. The results obtained in this manner are clearly presented in terms of the percent inhibition (%) afforded by the test compound as compared to the case where no compound was administered (i.e., the control or untreated animal where sorbitol levels normally rise from approximately 50–100 mM/g. tissue to as high as 400 mM/g. tissue in the 27-hour test period). In this manner, it was found that 3',4'-dihydro-spiro-[imidazolidine-4,1'(2'H)naphthalene]-5-one afforded a 52% reduction in the accumulated sorbitol levels of diabetic rats.

We claim:

1. A method for treating a diabetic host to prevent or alleviate diabetes-associated chronic complications arising in said host, which comprises administering to said diabetic host an effective amount of a compound selected from the group consisting of spiro-imidazolone bases of the formula:

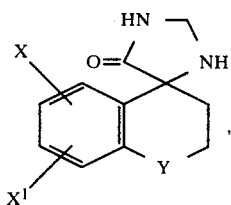

[I]

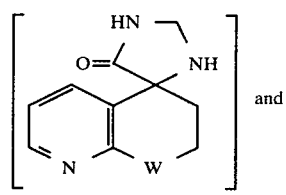 and

II

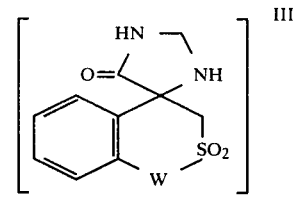

III and the pharmaceutically acceptable acid addition salts thereof, wherein

X is hydrogen and $X^1$ is hydrogen, fluorine, chlorine, bromine, lower alkyl or lower alkoxy; or X and $X^1$, when taken separately, are each chlorine, lower alkyl or lower alkoxy, and when taken together at adjacent positions of the molecule are —$OCH_2(CH_2)_nO$—;

Y is —$(CH_2)_n$—; and n is zero or one.

2. A method as claimed in claim 1 wherein the compound administered is a compound of the formula wherein X and $X^1$ are each hydrogen.

3. A method as claimed in claim 1 wherein the compound administered is a compound of the formula wherein X is hydrogen and $X^1$ is chlorine.

4. A method as claimed in claim 1 wherein the compound administered is 3',4'-dihydro-spiro-[imidazolidine-4,1'(2'H)-naphthalene]-5-one.

* * * * *